United States Patent
Tepper et al.

(10) Patent No.: US 12,333,660 B2
(45) Date of Patent: *Jun. 17, 2025

(54) METHODS AND DEVICES FOR INTRAOPERATIVE VIEWING OF PATIENT 3D SURFACE IMAGES

(71) Applicants: MONTEFIORE MEDICAL CENTER, Bronx, NY (US); ALBERT EINSTEIN COLLEGE OF MEDICINE, Bronx, NY (US); The New York City Health and Hospitals Corporation, New York, NY (US)

(72) Inventors: Oren Mordechai Tepper, New York, NY (US); Jillian Schreiber, New York, NY (US); Cesar Colasante, Bronx, NY (US)

(73) Assignees: Montefiore Medical Center, Bronx, NY (US); Albert Einstein College of Medicine, Bronx, NY (US); The New York City Health and Hospitals Corporation, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/210,435

(22) Filed: Jun. 15, 2023

(65) Prior Publication Data
US 2024/0161421 A1    May 16, 2024

Related U.S. Application Data

(63) Continuation of application No. 17/062,354, filed on Oct. 2, 2020, now Pat. No. 11,727,649, which is a
(Continued)

(51) Int. Cl.
*G06T 19/00*  (2011.01)
*A61B 5/00*   (2006.01)
(Continued)

(52) U.S. Cl.
CPC .......... *G06T 19/006* (2013.01); *A61B 5/0077* (2013.01); *A61B 34/10* (2016.02);
(Continued)

(58) Field of Classification Search
CPC ........ G06T 19/006; G06T 19/20; A61B 34/10
(Continued)

(56) References Cited

U.S. PATENT DOCUMENTS

| 5,715,836 A | 2/1998 | Kliegis et al. |
| 7,206,627 B2 | 4/2007 | Abovitz |

(Continued)

FOREIGN PATENT DOCUMENTS

| JP | 2014155207 A1 | 8/2014 |
| WO | 2014125789 A1 | 8/2014 |
| WO | 2015044184 A1 | 4/2015 |

OTHER PUBLICATIONS

Ayhan M, et al. "Skin marking in plastic surgery" *Plastic and reconstructive surgery* 2005, 115(5):1450-1451.
(Continued)

*Primary Examiner* — Peter Hoang
(74) *Attorney, Agent, or Firm* — Perkins Coie LLP

(57) ABSTRACT

Methods and devices are disclosed for intra-operative viewing of pre- and intra-operative 3D patient images.

20 Claims, 1 Drawing Sheet

Related U.S. Application Data continuation of application No. 15/761,832, filed as application No. PCT/US2016/053698 on Sep. 26, 2016, now Pat. No. 10,810,799.

(60) Provisional application No. 62/233,543, filed on Sep. 28, 2015.

(51) Int. Cl.
    A61B 17/00    (2006.01)
    A61B 34/10    (2016.01)
    A61B 34/20    (2016.01)
    A61B 90/00    (2016.01)
    G06T 7/00     (2017.01)
    G06T 7/62     (2017.01)
    G06T 7/68     (2017.01)
    G06T 7/73     (2017.01)
    G06T 19/20    (2011.01)
    G16H 50/50    (2018.01)

(52) U.S. Cl.
    CPC ............ *A61B 90/36* (2016.02); *A61B 90/361* (2016.02); *G06T 7/0014* (2013.01); *G06T 7/62* (2017.01); *G06T 7/68* (2017.01); *G06T 7/74* (2017.01); *G06T 19/20* (2013.01); *G16H 50/50* (2018.01); *A61B 2017/00792* (2013.01); *A61B 2034/105* (2016.02); *A61B 2034/2055* (2016.02); *A61B 2090/366* (2016.02); *A61B 2090/367* (2016.02); *A61B 2090/368* (2016.02); *A61B 2090/373* (2016.02); *A61B 2090/3979* (2016.02); *A61B 2505/05* (2013.01); *G06T 2200/04* (2013.01); *G06T 2207/10012* (2013.01); *G06T 2207/10028* (2013.01); *G06T 2207/10048* (2013.01); *G06T 2210/41* (2013.01)

(58) Field of Classification Search
    USPC .......................................................... 345/419
    See application file for complete search history.

(56) References Cited

U.S. PATENT DOCUMENTS

| | | | |
|---|---|---|---|
| 9,352,171 B2 | 5/2016 | Gertner | |
| 9,521,961 B2 | 12/2016 | Silverstein | |
| 10,810,799 B2 * | 10/2020 | Tepper | A61B 90/36 |
| 11,589,949 B1 | 2/2023 | Mills et al. | |
| 11,727,649 B2 * | 8/2023 | Tepper | G06T 19/20 |
| | | | 345/419 |
| 2001/0027263 A1 | 10/2001 | Zylka | |
| 2004/0068187 A1 | 4/2004 | Krause | |
| 2007/0135803 A1 | 6/2007 | Belson | |
| 2007/0154866 A1 | 7/2007 | Hall | |
| 2007/0208252 A1 | 9/2007 | Makower | |
| 2008/0159602 A1 | 7/2008 | Zank | |
| 2008/0159608 A1 | 7/2008 | Suetens et al. | |
| 2008/0300478 A1 | 12/2008 | Zuhars et al. | |
| 2010/0111364 A1 | 5/2010 | Iida | |
| 2010/0286995 A1 | 11/2010 | Pekar | |
| 2011/0160578 A1 | 6/2011 | Tripathi et al. | |
| 2012/0010533 A1 | 1/2012 | Arnett et al. | |
| 2012/0019511 A1 | 1/2012 | Chandrasekhar | |
| 2013/0113685 A1 | 5/2013 | Sugiyama et al. | |
| 2013/0172731 A1 | 7/2013 | Gole | |
| 2014/0031668 A1 | 1/2014 | Mobasser et al. | |
| 2014/0336461 A1 * | 11/2014 | Reiter | A61B 1/00193 |
| | | | 600/111 |
| 2015/0049081 A1 | 2/2015 | Coffey | |
| 2016/0228191 A1 | 8/2016 | Sabczynski | |
| 2016/0236009 A1 | 8/2016 | Sabczynski | |
| 2016/0345858 A1 | 12/2016 | Tromberg | |
| 2017/0042631 A1 | 2/2017 | Doo et al. | |
| 2017/0231714 A1 | 8/2017 | Kosmecki | |
| 2017/0258526 A1 | 9/2017 | Lang | |
| 2017/0270708 A1 | 9/2017 | Kutra | |
| 2017/0281367 A1 | 10/2017 | Ketchum et al. | |
| 2017/0325689 A1 | 11/2017 | Salah | |
| 2024/0177427 A1 * | 5/2024 | Cagan | G09B 23/28 |

OTHER PUBLICATIONS

Beale EW, et al. "Achieving predictability in augmentation mastopexy" *Plastic and reconstructive surgery* 2014, 133(3):284e-292e.

Chang, KN "The use of intraoperative grid pattern markings in lipoplasty" *Plastic and reconstructive surgery* 2004, 114(5):1292-1297.

Coleman SR "Facial augmentation with structural fat grafting" Clinics in plastic surgery 2006, 33(4):567-577.

Coleman SR "Structural fat grafting: more than a permanent filler" *Plastic and reconstructive surgery* 2006, 118(3 Suppl):108S-120S.

Extended European Search Report for European Patent Application No. 16852361.1. Mail Date: Jan. 9, 2020. 10 pages.

Granick MS, et al. "Surgical skin-marking techniques" *Plastic and reconstructive surgery* 1987, 79(4):573-580.

International Search Report and Written Opinion mailed Nov. 29, 2016 for International Application PCT/US2016/053698,7 pages.

Japanese Office Action, JP Appl. No. 2018-517201, dated Sep. 14, 2020, 4 pages.

Kim SS, et al. "Reconstruction of the irradiated orbit with autogenous fat grafting for improved ocular implant" *Plastic and reconstructive surgery* 2010, 126(1):213-220.

Mladick RA "The big six. Six important tips for a better result in lipoplasty" *Clinics in plastic surgery* 1989, 16(2):249-256.

Office Action mailed Jan. 9, 2023 in Canada Patent Application No. 3,038,648, 7 pages.

Partial Supplementary European Search Report mailed Sep. 30, 2019 in European Patent Application No. 16852361.1, 10 pages.

Sarifakioglu N, et al. "Skin marking in plastic surgery: a helpful suggestion." *Plastic and reconstructive surgery* 2003, 111(2): 946-947.

Sarifakioglu N, et al. "Skin marking in plastic surgery: color alternatives for marking" *Plastic and reconstructive surgery* 2003, 112(5):1500-1501.

Serra MP, et al. "A new flexible curved ruler to shorten the learning curve markings in the Hall-Findlay mammaplasty" Plastic and reconstructive surgery 2010, 126(1):31e-32e.

Shermak MA "Pearls and perils of caring for the postbariatric body contouring patient" *Plastic and reconstructive surgery* 2012, 130(4):585e-596e.

Tepper OM, et al. "The new age of three-dimensional virtual surgical planning in reconstructive plastic surgery" Plastic and reconstructive surgery 2012, 130(1): 192e-194e; author reply 194e-195e.

Tepper OM, et al. "Use of virtual 3-dimensional surgery in post-traumatic craniomaxillofacial reconstruction" *Journal of oral and maxillofacial surgery* 2011, 69(3):733-741.

Tepper OM, et al. "Virtual 3-dimensional modeling as a valuable adjunct to aesthetic and reconstructive breast surgery" American journal of surgery 2006, 192(4):548-551.

Xia, J. et al., "Computer-assisted three-dimensional surgical planning and simulation: 3D color facial model generation." Int. J. Oral Maxillofac.Surg., 2000: 29: pp. 2-10.

* cited by examiner

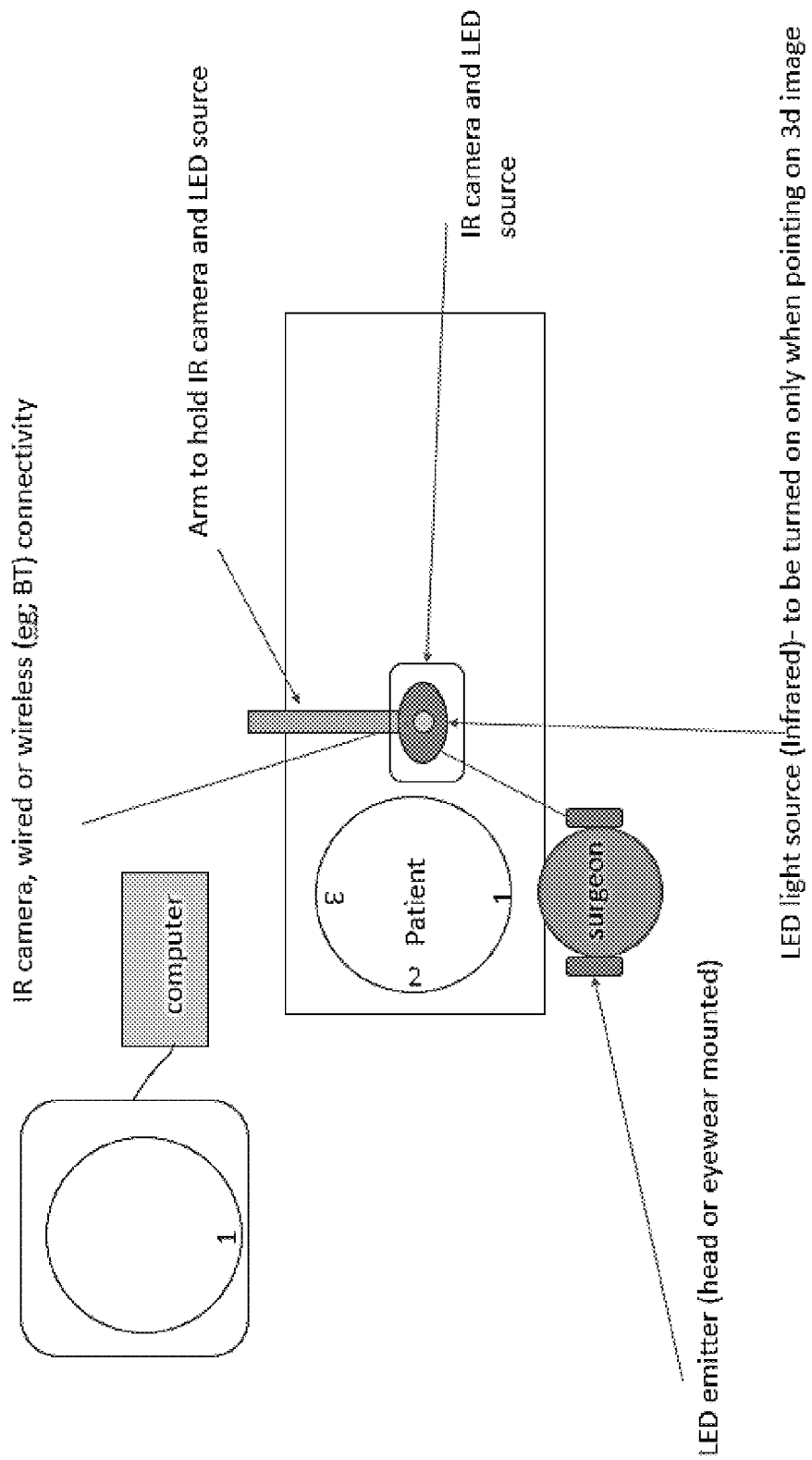

METHODS AND DEVICES FOR INTRAOPERATIVE VIEWING OF PATIENT 3D SURFACE IMAGES

CROSS-REFERENCE TO RELATED APPLICATION

This application is a continuation of U.S. patent application Ser. No. 18/210,435, filed Jun. 15, 2023, which is a continuation of U.S. patent application Ser. No. 17/062,354, filed Oct. 2, 2020, now U.S. Pat. No. 11,727,649, which is a continuation of U.S. patent application Ser. No. 15/761,832, filed Mar. 21, 2018, now U.S. Pat. No. 10,810,799, which is a Section 371 application of International Application No. PCT/US2016/053698, filed Sep. 26, 2016, which claims the benefit of U.S. Provisional Patent Application No. 62/233,543, filed on Sep. 28, 2015, the contents of each of which is herein incorporated by reference in its entirety.

FIELD OF THE INVENTION

The present invention relates to processes and apparatus involved in using three dimensional (3D) surface imaging of a patient in aesthetic and reconstructive surgery. This is accomplished through image acquisition of 3D images by any available method (e.g, laser surface, stereoscopy, surface scanning among others), processing the images to provide relevant data in the form of surgical map(s) or models, and projecting the images, map(s) and/or models onto the patient for guidance during surgery and/or displaying the images, map(s) or models to simulate the surgeon's point of view or another vantage point of interest. The images, map(s) and/or models can be displayed on a fixed or mobile screen, or a wearable device (i.e., head mounted) for operative viewing.

BACKGROUND OF THE INVENTION

Throughout this application various publications are referred to in brackets. Full citations for these references may be found at the end of the specification. The disclosures of these publications are hereby incorporated by reference in their entirety into the subject application to more fully describe the art to which the subject invention pertains.

3D imaging is a valuable asset in the planning, assistance and evaluation of various aesthetic and reconstructive surgical procedures. From 3D reconstructions of bony parts obtained by CAT scans, to reconstructions of body parts or prosthesis design for 3D printing, the spectrum of use and potential uses of 3D imaging is wide and extensive. Using this technology allows for better planning, provides the patient with an expected result during simulations and aids in performing the surgery with the aim of making surgeries safer, more precise and efficient.

Surgical markings play a crucial role in the planning of plastic surgery procedures [1-4]. Pre-operatively, a surgeon often will mark planned incisions and/or highlight regions of interest such as soft-tissue deficiency or excess [6-9]. However, despite the importance of markings as a guide in the operating room, these surgical markings are often imprecise and based on best estimation [5]. Autologous fat grafting (AFG) is one such procedure that heavily relies on surgical markings. At present, planning is limited to pre-operative assessment using physical examination and standard two-dimensional photographs, followed by traditional patient markings [10-12]. For instance, when assessing patients in need of autologous fat grafting, surgeons often base their markings on estimations of where volume deficiency exists and how much volume will be needed to correct the deficiency.

Facial and body photography is an important part of aesthetic surgery that contributes to intraoperative decision-making. As a result, most surgeons today mount pre-operative two dimensional (2D) photographs on the wall (or display on a screen) in the operating room (OR) as a reference to guide surgical judgment. While this has been customary among surgeons for decades, there are significant limitations to using only a few 2D "snapshots" when surgical decisions about facial contour need to be made.

The present invention provides systems and methods that use 3D surface imaging in aesthetics and reconstructive surgery providing improved intra-operative viewing of pre-operative and intra-operative patient images. This technique not only yields a more accurate approach to, e.g, fat grafting, but also provides a generalizable approach that can be applied to planning or execution of numerous other plastic surgical procedures.

SUMMARY OF THE INVENTION

Methods are provided for intraoperative viewing by a surgeon of three dimensional (3D) patient images, the methods comprising:
  processing 3D surface images or a simulated 3D virtual model of a patient to generate a surgical reference or plan to be used during surgery, and
  projecting the images or the model onto the patient and/or displaying the images or model for intraoperative viewing by the surgeon.

In addition, systems are provided for intraoperative viewing by a surgeon of three dimensional (3D) patient images, the systems comprising:
  a digital processor for processing 3D surface images or a simulated 3D virtual model of a patient to generate a surgical reference or plan to be used during surgery, and
  a projection unit for projecting the images or the model onto the patient and/or displaying the images or model for intraoperative viewing by the surgeon.

BRIEF DESCRIPTION OF THE DRAWINGS

FIG. 1. Example of an embodiment of a system for intraoperative viewing by a surgeon of three dimensional (3D) patient images.

DETAILED DESCRIPTION OF THE INVENTION

The present invention provides a method for intraoperative viewing by a surgeon of three dimensional (3D) patient images, the method comprising:
  processing 3D surface images or a simulated 3D virtual model of a patient to generate a surgical reference or plan to be used during surgery, and
  projecting the images or the model onto the patient and/or displaying the images or model for intraoperative viewing by the surgeon.

The 3D surface images can be pre-operative images of the patient and/or images acquired during surgery. Similarly, the simulated 3D virtual model can be a pre-operative model of the patient and/or the simulated 3D virtual model can use images acquired at different stages during the surgical procedure, optionally in combination with pre-operative images.

Intraoperative surface images can be compared with baseline images or a baseline surgical plan to assess operative results and the need for further surgical modification.

3D patient images can be acquired, for example, by 3D photography, laser surface scanning, stereoscopy or stereophotogrammetry, among other methods.

The step of processing the images can comprise an analysis of patient surface anatomy, such as for example, measurement of surface landmarks and/or planes, measurement of distance between landmarks and/or planes, volumetric measurements, and/or symmetry analysis. Processing the images can comprise comparison of one or more regions of a single image or comparison of one or more unique images.

The images or model can be projected onto the patient. The image or model can comprise a surgical map or guides that can be coded, projected or marked on the patient. The images or model can be projected using a projection system that can be portable or fixed.

The images or the model can be displayed, for example, on a screen or 3D viewer in the operating room. The 3D viewer can be, for example, a wall-mounted screen or a movable tower screen or wearable gear such as a head-mounted display.

Preferably, the orientation of the images or the model can be adjusted to correspond to the surgeon's vantage point with respect to the patient or another perspective of interest. Preferably, the orientation of the images or model adjusts to correspond to the orientation at which the surgeon views the patient or perspective of interest as the surgeon moves about during a surgical operation. The surgeon's vantage point with respect to the patient or perspective of interest can be determined, for example, using one or more infrared emitters attached directly or indirectly to the surgeon. A stationary infrared camera can be used to convert the infrared sources into location coordinates.

The invention can be used when surgery is performed on different locations on a patient, for example, on the face, head, neck, oral cavity or breast of the patient. The surgeon can be, for example, a plastic surgeon, a reconstructive surgeon, a head and neck surgeon, an oral surgeon, an otolaryngologist or a dermatologist.

The invention also provides a system for intraoperative viewing by a surgeon of three dimensional (3D) patient images, the system comprising:

a digital processor for processing 3D surface images or a simulated 3D virtual model of a patient to generate a surgical reference or plan to be used during surgery, and a projection unit for projecting the images or the model onto the patient and/or displaying the images or model for intraoperative viewing by the surgeon.

The system can also comprise, for example, one or more infrared emitters, an infrared camera, and/or apparatus for acquiring 3D images of the patient, such as for example a 3D camera. The projection unit can comprise a head-mounted device that displays the images or model. Preferably, the display of the images or model can be oriented to correspond to the orientation at which the surgeon views the patient or another perspective of interest.

In one embodiment, the present invention provides an intra-operative tool for a surgeon to view a patient's three dimensional (3D) images or models on a screen oriented to match the surgeon's vantage point. In other words, if the surgeon is standing at the head-of-bed, the 3D image or model on the screen will correspond to the same orientation at which the surgeon sees the patient on the table. This 3D image or model toggles according to where the surgeon moves about during the operation so that the view on the screen continues to match the surgeon's vantage point.

In order to orient the 3D image or model to the surgeon-view, a surgeon can wear a head-mounted tracking device. At the start of the operation, landmarks and reference planes are established to the patient's 3D image or model. As the surgeon moves around the patient in the operating room (OR), the 3D image or model rotates to mirror the surgeon's view. For any view that becomes relevant during surgery, the surgeon can now look to a screen and see the corresponding 3D image or model for a seamless reference to guide surgical decision-making.

3D Display. The 3D display component allows viewing, manipulation and analysis of 3D images as well as providing the surgeon's point of view for the assistants in surgical procedures. This can be achieved, e.g., by using infrared light (IR) tracking technology, including, for example, an IR camera, two or more IR emitting sources to be positioned on the surgeon, for example on protective eyewear or on a head mount, a computer to analyze the motion and render the corresponding images and one or more monitors to display the corresponding image(s). Optional devices include a voice sensor for commands, foot pedals as switch, and an IR light source surrounding the camera facing the surgeon among others.

Virtual 3D model(s) of the patient's area of interest can be captured and processed prior to the procedure or during the procedure if required, these images can be imported into a computer system connected to the IR camera. This coupling can be made either wired or by wireless connection. Modifications such as markings, and desired results among other modifications can also be imported into the system.

IR light sources stemming from, e.g., the head mount or surgeon's protective eyewear can be captured by an IR camera; with these coordinates the software can reproduce the view of the surgeon on the 3D model, which can be displayed in the monitor(s). At least two modalities can be offered, continuous view, which will give an infinite amount of views that will rotate, tilt and move the 3D model or image according to the surgeon's position relative to the patient and IR camera, and preset view, which analyzes the coordinates within ranges of location to render predetermined points of view to be displayed on the monitor(s). As an optional component there can be an IR emitter surrounding the camera that by default can be on the off position; once activated, the light source from the surgeon's location will be turned on. The emitter surrounding the camera can provide light waves that bounce from reflective surfaces. As an example, a finger covered in a white glove can serve as a reflective surface. Additionally reflective objects such as metallic surgical instruments or pointers with reflective surfaces can be used. These coordinates can be used to point, mark, manipulate, select, accept or cancel options on the monitor as would a computer mouse cursor.

3D Projection onto the patient. The projection component can be a two dimensional projection based on 3D virtual models or images that serves as a surgical road map. These can be defined by, e.g., landmarks, incision lines, tracings (e.g. for z-plasty), areas of interest, helpers as rulers, protractors, map of lines of tension, and/or volume projections amongst other guides onto patients to be used as a template or map to assist, guide and evaluate surgical procedures.

The systems can function by having surgical map(s) or models made a priori that depicts the relevant guides that can be projected on the patient. This component of the process is comprised of at least but not limited to a video projector, a mounting bracket for an overhanging light source and/or stand, and at least one map of the area to be addressed. The mounting bracket can come in different shapes and forms but will allow rotation of the projector. The projection will be oriented onto the patient to allow accurate overlapping of the image, map or model on the patient.

A controller can be added that can be physical or voice activated to allow toggling between different projections, different maps in different stages of the procedure(s) and/or landmarks among other functions.

This invention will be better understood from the Experimental Details, which follow. However, one skilled in the art will readily appreciate that the specifics discussed are merely illustrative of the invention as described more fully in the claims that follow thereafter.

EXPERIMENTAL DETAILS

Creation of a 3D Topographical Surgical Map

Patients undergoing autologous fat grafting (AFG) for facial asymmetry had pre-operative 3D photographs taken using a handheld camera (VECTRA® H1, Canfield Scientific, Inc© 2013). Facial asymmetry was analyzed by creating a mid-sagittal plane, which bisected the 3D model into two distinct hemi-faces. The reference hemi-face was reflected onto the defect side creating a new hemi-composite, which served as the reference 3D model. The reference model was then overlayed using Canfield VECTRA® Analysis Module (VAM) software on a patient image. Next, a color map was generated, which outlined the differences between the two surfaces. The resulting color map was a well-circumscribed region of volume deficiency colored according to the relative distances between the normal and abnormal hemi-face. This difference in projection is represented by a smooth color gradient.

To create a digital 3D topographic surgical map, contour curves were generated on the 3D color maps. Analogous to topographic mapping of geographic landscapes, the contour curves at discrete projection values represent the 3D surface. To generate the contour curves, the minimum sensitivity of the color map was adjusted and traced. Tracings were made at 1 mm, 3 mm, 5 mm, and 7 mm, until the threshold exceeded the topographic change. A composite of the individual tracings generated the final topographic map. The map was enhanced with landmarks on key facial structures to ensure proper scale and alignment when projected onto the patient.

Patient Image Projection

The digital 3D topographical map was then used as a template for pre-operative patient markings and provided the surgeon with the relative location and degree of volume deficiency. The maps were saved as a pdf file, uploaded onto a mobile platform (iPhone 5s), and projected using a handheld, smart phone compatible LED Pocket Projector (AAXA Technologies, USA). The iPhone-projector construct was secured to an overhead operating room light for stable, hands-free, projection. The projector-light platform was positioned such that key landmarks on the projected map aligned on the patient. By using this overlay as a guide, colored marking pens assigned to specific projection values were then used to trace the map.

Following this, patients underwent autologous fat harvesting and transfer using standard techniques. Fat was injected according to the region and degree of deficiency as indicated by the topographic map, beginning centrally in the most deficient region. The map was also projected onto the patient intra-operatively for further guidance.

Discussion

This report provides a description of soft-tissue computer surgical planning used to guide surgical marking. Rather than relying on surgeon assessment alone, 3D surface scanning technology was applied to perform an objective symmetry analysis. The virtual plan was translated to the OR using a projected image.

The use of virtual surgical planning (VSP) for skeletal-based facial reconstruction has been described [13, 15]. However, in these cases, the computer simulation was transferred to the OR in the form of images, printed jigs, cutting guides, and pre-bent plates.

In this report, 2 mm projection intervals were arbitrarily chosen; however, the interval can be determined by the size of the defect and type of reconstruction; i.e. smaller defects require tighter intervals for more precise intervention, and larger defects require wider intervals. In addition, the exact volume of fat required to affect the desired change in projection is variable. This change in projection depends on multiple factors, including skin quality, tissue elasticity, and fat resorption.

Although this example focuses on AFG, other areas of plastic surgery could benefit from the use of a similar soft-tissue surgical roadmap. The concept of topographic mapping is an ideal method of representing 3D contours through 2D marking on the skin surface. Projection offers a fast and reliable method of transferring a digital surgical plan that can be easily reproduced intra-operatively without breaking sterility. Procedures that target body contours, such as injection of fillers, breast surgery, or liposuction, rely heavily on pre operative surgical markings to identify target areas. It is conceivable that a pre-fabricated roadmap developed on the computer can be projected and traced on the skin surface, offering an increasingly precise and effective approach to surgical marking and placement of incisions.

This is the first report that describes the use of pre-operative markings projected onto the patient as a 3D image. This provides the surgeon with a soft tissue surgical plan that precisely describes the relevant anatomy and may illuminate areas not appreciated on physical exam. By referencing markings generated by computer analysis and surgical simulation, the surgeon has a topographic map that is a simplified translation of the complex 3D contour. This provides an easy-to-follow guide tailored to the patient's unique volume needs which are often not appreciated on standard photographs.

REFERENCES

1. Granick M S, Heckler F R, Jones E W: Surgical skin-marking techniques. *Plastic and reconstructive surgery* 1987, 79(4):573-580.
2. Ayhan M, Silistreli O, Aytug Z, Gorgu M, Yakut M: Skin marking in plastic surgery. *Plastic and reconstructive surgery* 2005, 115(5):1450-1451.
3. Sarifakioglu N, Yuksel A, Cigsar B, Aslan G: Skin marking in plastic surgery: color alternatives for marking. *Plastic and reconstructive surgery* 2003, 112(5):1500-1501.
4. Sarifakioglu N, Terzioglu A, Cigsar B, Aslan G: Skin marking in plastic surgery: a helpful suggestion. *Plastic and reconstructive surgery* 2003, 111(2):946-947.
5. Chang K N: The use of intraoperative grid pattern markings in lipoplasty. *Plastic and reconstructive surgery* 2004, 114(5):1292-1297.

6. Serra M P, Longhi P, Rao G S: A new flexible curved ruler to shorten the learning curve markings in the Hall-Findlay mammaplasty. *Plastic and reconstructive surgery* 2010, 126(1):31e-32e.
7. Beale E W, Ramanadham S, Harrison B, Rasko Y, Armijo B, Rohrich R J: Achieving predictability in augmentation mastopexy. *Plastic and reconstructive surgery* 2014, 133(3):284e-292e.
8. Shermak M A: Pearls and perils of caring for the post-bariatric body contouring patient. *Plastic and reconstructive surgery* 2012, 130(4):585e-596e.
9. Mladick R A: The big six. Six important tips for a better result in lipoplasty. *Clinics in plastic surgery* 1989, 16(2):249-256.
10. Coleman S R: Facial augmentation with structural fat grafting. *Clinics in plastic surgery* 2006, 33(4):567-577.
11. Coleman S R: Structural fat grafting: more than a permanent filler. *Plastic and reconstructive surgery* 2006, 118(3 Suppl):108S-120S.
12. Kim S S, Kawamoto H K, Kohan E, Bradley J P: Reconstruction of the irradiated orbit with autogenous fat grafting for improved ocular implant. *Plastic and reconstructive surgery* 2010, 126(1):213-220.
13. Tepper O, Hirsch D, Levine J, Garfein E: The new age of three-dimensional virtual surgical planning in reconstructive plastic surgery. *Plastic and reconstructive surgery* 2012, 130(1):192e-194e; author reply 194e-195e.
14. Tepper O M, Small K, Rudolph L, Choi M, Karp N: Virtual 3-dimensional modeling as a valuable adjunct to aesthetic and reconstructive breast surgery. *American journal of surgery* 2006, 192(4):548-551.
15. Tepper O M, Sorice S, Hershman G N, Saadeh P, Levine J P, Hirsch D: Use of virtual 3-dimensional surgery in post-traumatic craniomaxillofacial reconstruction. *Journal of oral and maxillofacial surgery: official journal of the American Association of Oral and Maxillofacial Surgeons* 2011, 69(3):733-741.

What is claimed is:

1. A method, comprising:
   providing instructions for displaying, via a wearable device, a dataset on a patient,
   wherein:
      the dataset is based at least in part on a three-dimensional (3D) surface image of the patient or is based at least in part on a 3D model of the patient's surface anatomy,
      the dataset is representative of an actual contour curve and a desired contour curve of the patient's surface anatomy, and
      the actual and desired contour curves of the dataset (a) are aligned with each other and (b) are alignable with the patient such that the actual and desired contour curves of the dataset are aligned with landmarks on the patient's surface anatomy.

2. The method of claim 1, wherein the wearable device includes a head-mounted display.

3. The method of claim 1, further comprising displaying, via the wearable device, the dataset on the patient.

4. The method of claim 3, wherein displaying the dataset on the patient includes projecting, via the wearable device, the dataset on the patient.

5. The method of claim 1, wherein the dataset includes predetermined discrete interval values that represent (i) the actual contour curve of the patient's surface anatomy and (ii) intended changes to the actual contour curve of the patient's surface anatomy to achieve the desired contour curve.

6. The method of claim 5, wherein the predetermined discrete interval values are based at least in part on (i) a type of intervention, (ii) a region of the patient's surface anatomy corresponding to the actual contour curve or to the desired contour curve, or (iii) a combination thereof.

7. The method of claim 1, wherein the 3D surface image of the patient is a preoperative 3D surface image of the patient, or the 3D model of the patient's surface anatomy is a preoperative 3D model of the patient's surface anatomy.

8. The method of claim 1, wherein the 3D surface image of the patient is a first intraoperative image of the patient, or the 3D model of the patient's surface anatomy is based at least in part on a second intraoperative image of the patient.

9. The method of claim 1, wherein providing the instructions for displaying the dataset on the patient includes providing the instructions such that the dataset is intraoperatively alignable with the patient.

10. The method of claim 1, wherein providing the instructions for displaying the dataset on the patient includes providing instructions for displaying, via the wearable device, the dataset on the patient such that the dataset is oriented to correspond to a viewer's vantage of the patient.

11. The method of claim 1, wherein providing the instructions for displaying the dataset on the patient includes adjusting an orientation of the dataset such that the orientation of the dataset, when displayed on the patient via the wearable device, corresponds to a viewer's vantage of the patient.

12. The method of claim 11, wherein adjusting the orientation of the dataset includes rotating, tilting, or translating the dataset such that, when the dataset is displayed on the patient via the wearable device, the actual and desired contour curves of the dataset are aligned with the landmarks on the patient's surface anatomy.

13. The method of claim 11, wherein adjusting the orientation of the dataset includes continuously adjusting the orientation of the dataset according to the viewer's vantage of the patient as the viewer moves about the patient.

14. The method of claim 11, wherein adjusting the orientation of the dataset includes adjusting the orientation of the dataset to a predetermined point of view corresponding to a range of locations that includes a current location of the viewer relative to the patient.

15. A system, comprising:
   a dataset generated based at least in part on a three-dimensional (3D) surface image of a patient or based at least in part on a 3D model of the patient's surface anatomy, wherein the dataset is representative of an actual contour curve and a desired contour curve of the patient's surface anatomy, and wherein the actual and desired contour curves of the dataset (a) are aligned with each other and (b) are alignable with the patient such that the actual and desired contour curves of the dataset are aligned with landmarks on the patient's surface anatomy; and
   a controller configured to provide instructions for displaying, via a wearable device, the dataset on the patient.

16. The system of claim 15, further comprising the wearable device, and wherein the wearable device includes a head-mounted display.

17. The system of claim 15, wherein the instructions for displaying the dataset on the patient include instructions for displaying, via the wearable device, the dataset on the patient such that the dataset is oriented to correspond to a viewer's vantage of the patient.

18. The system of claim 15, wherein:
- the controller is configured to adjust an orientation of the dataset such that the orientation of the dataset, when displayed on the patient via the wearable device, corresponds to a viewer's vantage of the patient; and
- to adjust the orientation of the dataset, the controller is configured to tilt, rotate, or translate the dataset such that, when the dataset is displayed on the patient via the wearable device, the actual and desired contour curves of the dataset are aligned with the landmarks on the patient's surface anatomy.

19. The system of claim 18, wherein, to adjust the orientation of the dataset, the controller is configured to continuously adjust the orientation of the dataset according to the viewer's vantage of the patient as the viewer moves about the patient.

20. The system of claim 18, wherein, to adjust the orientation of the dataset, the controller is configured to adjust the orientation of the dataset to a predetermined point of view corresponding to a range of locations that includes a current location of the viewer relative to the patient.

\* \* \* \* \*